United States Patent
Sorger et al.

(10) Patent No.: US 6,921,487 B2
(45) Date of Patent: Jul. 26, 2005

(54) REMOVAL OF ZINC SALTS FROM NONAQUEOUS SYNTHESIS SOLUTIONS COMPRISING ZINC ALKOXIDES OR ZINC AMIDES

(75) Inventors: Klas Sorger, München (DE); Hermann Petersen, Burghausen (DE); Jürgen Stohrer, Pullach (DE)

(73) Assignee: Consortium für elektrochemische Industrie GmbH & Co. KG, Munich (DE)

(*) Notice: Subject to any disclaimer, the term of this patent is extended or adjusted under 35 U.S.C. 154(b) by 163 days.

(21) Appl. No.: 10/639,804

(22) Filed: Aug. 12, 2003

(65) Prior Publication Data

US 2004/0089613 A1 May 13, 2004

(30) Foreign Application Priority Data

Aug. 14, 2002 (DE) .......................... 102 37 274

(51) Int. Cl.⁷ .......................... B01D 21/01; C07F 3/06
(52) U.S. Cl. ........................ 210/729; 556/118
(58) Field of Search .......................... 210/729; 556/118

(56) References Cited

U.S. PATENT DOCUMENTS 4,624,704 A * 11/1986 Byeseda ..................... 210/688
4,678,584 A    7/1987 Elfline ....................... 210/719
5,762,807 A    6/1998 Straten ....................... 210/716

FOREIGN PATENT DOCUMENTS

EP          526997       2/1993

OTHER PUBLICATIONS

Palomo Claudio et al., Tetrahedron Letters, vol. 31 No. 15, 1990, p. 2205–8.
Marvin M. Hansen et al., Organometallics, vol. 6, 1987, p. 2069–74.
A. Fürstner, Synthesis 1989, p. 571.
C. Palomo et al., Tetrahedron Lett. 1990, 31, p. 6425.
C. Palomo et al., Tetrahedron Lett. 1990, 31, p. 2205.
K. Soai, T. Shibata, Comprehensive Asym–metric Catalysis, vol. II, Berlin,1999, pp. 911–922.
Heathcocle et al., Organometallics, 1987, 6, p. 2069.

* cited by examiner

*Primary Examiner*—Porfirio Nazario-Gonzalez
(74) *Attorney, Agent, or Firm*—Colland & Roe, P.C.

(57) ABSTRACT

A process for removing zinc from organic solutions comprising zinc alkoxides or zinc amides, includes admixing the solution with an alkylating, arylating, acylating or silylating agent in the presence of a precipitating reagent having at least two nitrogen donors and subsequently removing the precipitated solid.

10 Claims, No Drawings

REMOVAL OF ZINC SALTS FROM NONAQUEOUS SYNTHESIS SOLUTIONS COMPRISING ZINC ALKOXIDES OR ZINC AMIDES

BACKGROUND OF THE INVENTION

1. Field of the Invention

The present invention relates to a process for removing zinc salts from nonaqueous synthesis solutions comprising zinc alkoxides or zinc amides.

2. The Prior Art

Organozinc compounds are industrially significant organometallic compounds for preparing synthetic building blocks for active pharmaceutical ingredients, scents and plant protectants.

For example, α-bromozinc esters, prepared by reaction of α-bromocarboxylic esters with zinc, find use in reactions with electrophilic substrates, for example aldehydes, ketones or imines (Reformatsky syntheses). Asymmetric additions of dialkyl- or diarylzinc compounds to aldehydes or ketones for preparing chiral alcohols as synthetic intermediates are of increasing industrial interest.

When organozinc compounds are used in industrial synthetic processes, the workup results in inorganic salts containing zinc ions or zinc salts having additional organic constituents which are typically dissolved, suspended or emulsified in an aqueous medium. As heavy metal ions, especially as a constituent of aqueous or aqueous-organic wastewater, zinc ions are generally regarded as environmentally polluting, because they cannot be destroyed, merely chemically changed, for example by conversion to soluble or insoluble zinc compounds or by reduction to the elemental state. Aqueous solutions, suspensions or emulsions comprising zinc ions therefore have to be freed of zinc ions to a legally stipulated residual content before purification, incineration, landfill disposal or disposal as appropriate wastewater.

To reduce the zinc ion content in aqueous solutions, suspensions or emulsions, in some cases comprising organic constituents, as obtained, for example, after workup of synthesis solutions or reaction mixtures in industrial preparative processes using organozinc compounds, various procedures of precipitating sparingly soluble zinc salts and removing the sparingly soluble salts from the aqueous phase are known.

U.S. Pat. No. 4,678,584 describes a method for removing zinc ions from wastewaters by precipitating as sparingly soluble sulfides by treating the wastewaters with trithiocarbonate.

U.S. Pat. No. 5,762,807 discloses a process for precipitating complexed and noncomplexed heavy metals, for example zinc, from aqueous media by treating with an aqueous mixture of polysulfide and polysulfane compounds.

EP 0526997 discloses the removal of dissolved chelated zinc ions from aqueous solutions in a multistage process by precipitating sparingly soluble zinc salts.

However, the prior art processes have a series of disadvantages. In the existing processes, the heavy metal salts are in principle precipitated from aqueous solutions, as occur after hydrolytic workup of the synthesis solutions or reaction mixtures when using organozinc compounds. This means that a medium comprising aqueous zinc ions is first generated, from which the zinc salts have to be removed again in a subsequent step by precipitation, and that the wastewaters obtained after the removal of the zinc salts have to be purified. In addition, this procedure associated with considerable cost and inconvenience is very uneconomic. For economic and ecological reasons, a significantly more desirable process would generate no aqueous phase at all and no wastewater containing zinc ions.

In addition, after removal of the precipitated heavy metal salts, wastewaters are typically obtained which contain organic constituents and organic, water-miscible solvents to a not inconsiderable extent, for example tetrahydrofuran which serves as a solvent in organozinc syntheses. For economic reasons and to reduce the amounts of waste, especially on application on the industrial scale, recovery of the solvent used from the aqueous phase, for example by extraction or distillation, is necessary, although this is again associated with a considerable financial and technical burden.

There is also the possibility that the reaction products prepared or their solutions, which may complex with the zinc ions via functional hydroxyl, carboxyl, thio or amino groups, may decompose or be contaminated by undesired by-products on treatment with the precipitating agent (e.g. sulfide, polysulfide, polysulfane, trithiocarbonate) under the conditions which are necessary for precipitating and removing the zinc salts. This is especially as a result of thermal stress or long reaction times, and thus the quality of the products prepared is reduced and the economic viability of the overall preparative process is impaired.

The complexing of the zinc salts via functional groups, e.g. oxy, amine, amide or thio groups, of the products prepared by organozinc synthesis leads to some or all of the zinc as an impurity to be removed remaining in solution.

In addition, the precipitation of the sparingly soluble zinc salts according to U.S. Pat. No. 5,762,807 and EP 0526997 entails a series of further process steps. For example these further steps include the setting of a predetermined pH by adding acid or base, the addition of further reagents or filtering assistants or the thermal treatment of the precipitate, in order to achieve better filterability. The entire precipitation process known from the prior art makes special plants necessary, which leads to considerable time demands and costs, and impairs the economic viability of the existing precipitation processes, especially when used on the industrial scale.

The zinc salts precipitated from aqueous medium, e.g. zinc hydroxide, zinc carbonate or zinc sulfide compounds or mixtures thereof are often difficult to filter and, after removal by filtration or centrifugation, contain considerable amounts of water. Since the precipitated zinc salts have to be disposed of in landfills or fed to zinc recycling, the economic viability of the entire process, especially when carried out on the industrial scale, is compromised by the considerable economic demands of transporting voluminous zinc salts having a high water content or drying or otherwise treating the zinc salts. None of the prior art processes makes it possible to directly remove zinc salts from nonaqueous synthesis or reaction solutions comprising zinc compounds without preceding aqueous workup, or under nonaqueous precipitation conditions or using nonaqueous precipitation media.

SUMMARY OF THE INVENTION

It is therefore an object of the present invention to provide a simple, economic and universally applicable process for removing zinc present as zinc ions or zinc salts from synthesis solutions or reaction solutions comprising zinc compounds which solves the known problems of the prior art.

This object has been achieved by developing a process which allows zinc to be quantitatively precipitated out of synthesis solutions comprising zinc alkoxides or zinc amides after silylation, acylation, alkylation or arylation in the presence of a compound containing at least two nitrogen donors under nonaqueous conditions.

The present invention therefore provides a process for removing zinc from organic solutions comprising zinc alkoxides or zinc amides,
which comprises
admixing the solution with an alkylating, arylating, acylating or silylating reagent in the presence of a precipitating reagent having at least two nitrogen donors and subsequently removing the precipitated solid.

The process according to the invention is carried out in an organic solvent.

Useful solvents for the process according to the invention are all inert solvents suitable for the reaction of organozinc compounds. An example of a summary of suitable solvents for organozinc reactions is contained in A. Fürstner, *Synthesis* 1989, p. 571.

Preferred solvents are hydrocarbons, ethers, carboxylic esters, amines, amides, ketones, polar aprotic solvents, halogenated hydrocarbons or mixtures of the solvents mentioned, in particular hydrocarbons, carboxylic esters and linear or cyclic mono- and polyethers.

Particularly preferred solvents are in particular benzene, toluene, ethylbenzene, propylbenzene, isopropylbenzene, butylbenzene, xylene, xylene isomer mixtures, trimethylbenzene, pentane, hexane, octane, isooctane, nonane, nonane fractions, cyclohexane, cycloheptane, cyclooctane, dimethylcyclohexane, ethylcyclohexane, propylcyclohexane, butylcyclohexane, petroleum and paraffin, diethyl ether, dipropyl ether, dibutyl ether, diisopropyl ether, methyl tert-butyl ether, dimethoxymethane, diethoxymethane, dimethoxyethane, diethoxyethane, diethylene glycol dimethyl ether, diethylene glycol diethyl ether, diethylene glycol dipropyl ether, diethylene glycol dibutyl ether, triethylene glycol dimethyl ether, triethylene glycol diethyl ether, triethylene glycol dibutyl ether, tetrahydrofuran, 2-methyltetrahydrofuran, 2,5-dimethyltetrahydrofuran, 2,5-dimethoxytetrahydrofuran and 1,4-dioxane, methyl, ethyl, n-propyl, isopropyl, n-butyl, isobutyl, t-butyl, n-hexyl, n-pentyl and isopentyl acetate, propionate and butyrate, 2-ethoxyethyl acetate, pyridine, -acetylpyrrolidine, N-acetylpyrrole, N-acetylsuccinimide, tetramethylurea, N,N"-dimethylethyleneurea, tetramethylguanidine, acetone, methyl ethyl ketone, diethyl ketone, isopropyl methyl ketone, isopropyl ethyl ketone, acetonitrile, propionitrile, butyronitrile, dimethylformamide, diethylformamide, dimethylacetamide, diethylacetamide, 1-methyl-2-pyrrolidone, dimethyl sulfoxide and methylene chloride, in particular hexane, ethyl acetate, tetrahydrofuran and 1,4-dioxane.

The solvents or their mixtures are suitable for all steps of the process according to the invention.

The synthetic intermediates initially formed in the reaction of organozinc compounds with substrates in suitable organic solvents are halozinc alkoxides or halozinc amides, or organozinc alkoxides or organozinc amides (zinc alkoxides or zinc amides)

In one possible embodiment of the process, the removal according to the invention of zinc from solutions comprising halozinc alkoxides or halozinc amides is carried out.

A typical embodiment of the process according to the invention is the removal of zinc from organic synthesis solutions of Reformatsky reactions.

In a further typical embodiment of the process, the removal according to the invention of zinc from solutions comprising organozinc alkoxides or organozinc amides is carried out, especially from those organic solutions which are formed in the reaction of alkylzinc or arylzinc compounds with electrophilic substrates, familiar as alkylation or arylation reactions of carbonyl compounds.

In the process according to the invention, the zinc alkoxides or zinc amides as synthesis solutions or reaction solutions comprising synthetic intermediates are reacted directly with suitable silylating, acylating, alkylating or arylating reagents to form the desired reaction product by reacting the alkoxide or amide with the silylating, acylating, alkylating or arylating agent and a zinc salt, e.g. zinc dihalide.

The products in the form of a silyl-, acyl-, alkyl- or aryloxy compound or silyl-, acyl-, alkyl- or arylamine compound and the zinc salt are typically dissolved in the organic solvent or partly or entirely suspended. In this case the product may in some cases complex with the zinc salt via functional groups, e.g. oxy, amine, amide or thio groups, and some or all of the zinc salt consequently remains in solution.

To remove the partly or completely dissolved zinc from the organic synthesis solutions in the process according to the invention, a compound containing at least two nitrogen donors is added as the precipitating reagent (hereinafter called precipitating reagent).

To remove the zinc from the synthesis solutions comprising zinc alkoxides or zinc amides in the process according to the invention, the reagents used may be added in any desired sequence.

It is also possible to initially charge the silylating, acylating, alkylating or arylating reagent or agent when preparing the zinc alkoxide or zinc amide. In this case, the zinc alkoxide or zinc amide formed reacts directly with the silylating, acylating, alkylating or arylating reagent or agent to form the desired product and a zinc salt.

It is also possible to add the precipitating reagent directly to the synthesis solution comprising zinc alkoxides or zinc amides as synthetic intermediates before the further reaction with the silylating, acylating, alkylating or arylating reagent.

The precipitating reagent according to the invention utilizes the chelate effect to form a solid with the zinc in the form of a zinc complex which is sparingly soluble in the organic solvent used for the synthesis, stable and readily removable, and makes it possible to virtually completely remove the zinc from the organic reaction solution. The chelate effect of the precipitating reagent according to the invention completely displaces the reaction product which had previously been complexed to the zinc salt.

When no compounds which are capable of chelating are used, for example compounds which only have one nitrogen donor (e.g. monoamines, for example triethylamine), the precipitation and removal of the zinc salts only succeeds incompletely (see comparative examples), if at all. This makes further, costly and inconvenient steps necessary for complete removal of the zinc, which have a considerable adverse effect on the economic viability of the overall process.

The precipitated zinc salt complex can subsequently be removed under suitable conditions, for example filtration or centrifugation, optionally at reduced temperature.

The mixtures obtained after removal of the precipitated zinc salts comprise the product prepared (desired synthetic product) and organic solvent.

The zinc is precipitated by the precipitating reagent in the process according to the invention virtually quantitatively, so that the reaction product prepared and the solvent removed from it have virtually no zinc residues.

The products prepared can be isolated by known, customarily used methods such as extraction, distillation, crystallization or by means of chromatographic methods. Due to its very high purity, the crude product obtained after removing the solvent can be used directly in subsequent reactions and conversions.

The products or solutions of products obtained after removing the zinc salts in the process according to the invention have a very low content of zinc ions of from 0.05 to 700 ppm, typically from 0.1 to 200 ppm. The products are used in further synthetic processes, and a further removal of zinc ions may optionally take place.

A typical embodiment of the process according to the invention is the removal of zinc from reaction solutions of Reformatsky reactions. The reaction of reactive halogen compounds, in particular α-halocarbonyl compounds, with electrophilic substrates, e.g. aldehydes, ketones, imines, nitriles, carboxylic anhydrides and chlorides, lactones, orthoformates, formates, epoxides, azirines, aminals and nitrones (substrates) in the presence of elemental zinc metal (Reformatsky reaction) results in the formation, in a first step, of halozinc alkoxides or halozinc amides as synthetic intermediates. This is due to the reaction of organozinc compounds (Reformatsky reagents), in particular α-halozinc esters, with the substrates. These synthetic intermediates containing zinc ions are dissolved or completely or partly suspended in the organic solvent used.

In a typical embodiment of the process according to the invention, a halozinc alkoxide is formed, for example by reaction of methyl a-bromozinc acetate with benzaldehyde in ethyl acetate as solvent and subsequently reacted with trimethylchlorosilane. The zinc bromide chloride formed in the reaction initially remains completely in solution as a result of complexing. When the same reaction is carried out in tetrahydrofuran as the solvent, there is partial precipitation of the zinc salt or zinc salt-product complex.

After the addition of a precipitating reagent according to the invention, for example piperazine, a sparingly soluble zinc salt-piperazine complex precipitates out.

C. Palomo et al. (C. Palomo, J. M. Aizpurua, M. C. Lopez, N. Aurrekoetxea, M. Oiarbide *Tetrahedron Lett*. 1990, 31, p. 6425 and C. Palomo, J. M. Aizpurua, M. C. Lopez, N. Aurrekoetxea, *Tetrahedron Lett*. 1990, 31, p. 2205) disclose the reaction of zinc alkoxides formed as intermediates with trimethylchlorosilane as silylating reagent in tetrahydrofuran as solvent. However, means of removing zinc salts formed, which would provide an industrial-scale, economic and environmentally friendly synthesis, were not described.

A further typical embodiment of the process according to the invention is the removal of zinc from reaction solutions which result from the reaction of dialkylzinc or diarylzinc compounds with electrophilic substrates, in particular with aldehydes or ketones. In these reactions, familiar as alkylation or arylation reaction of carbonyl compounds (e.g. K. Soai, T. Shibata in *Comprehensive Asymmetric Catalysis*, E. N. Jacobsen, A. Pfalz, H. Yamamoto, eds., Volume II, Springer, Berlin 1999, p. 911–922), the reaction of the organozinc compounds with the substrates results in organozinc alkoxides or organozinc amides as synthetic intermediates. These synthetic intermediates containing zinc ions are dissolved or partly or completely suspended in the organic solvent used for the reaction.

In a typical embodiment of the process according to the invention, the synthesis solutions or reaction solutions comprising the organozinc alkoxides or organozinc amides as synthetic intermediates are reacted directly in a subsequent step with suitable silylating, acylating, alkylating and arylating reagents to form the desired reaction product and a zinc compound, e.g. organo zinc halide. This is done by reacting the alkoxide or amide with the silylating, acylating, alkylating or arylating agent and a The desired synthesis product, a silyl-, acyl-, alkyl- or aryloxy compound or silyl-, acyl-, alkyl- or arylamine compound, and the zinc compounds are dissolved or partly or completely suspended in the organic solvent.

After the addition of a precipitating reagent according to the invention, e.g. piperazine, a sparingly soluble zinc salt-piperazine complex precipitates out.

Heathcock et al. (M. M. Hansen, P. A. Bartlett, C. H. Heathcock, *Organometallics*, 1987, 6, p. 2069) disclose, for example, the preparation of complexes of an ethylzinc enolate and the diamines (–) sparteine and N,N,N',N'-tetramethylethylenediamine by adding the diamines to the zinc enolate in the solvents tetrahydrofuran, diethyl ether and toluene. On reaction with benzaldehyde, the complexes of ethylzinc enolate and diamine remain in solution and, after reaction, the reaction mixture was hydrolyzed by adding aqueous ammonium chloride solution to obtain the zinc in dissolved form in the aqueous phase.

However, in the process according to the invention, the surprisingly highly effective removal of the zinc succeeds precisely by the combination of measures of the presence of a silylating, acylating, alkylating or arylating reagent and of a precipitating reagent having at least two nitrogen donors in an organic solvent.

This converts the zinc alkoxide or zinc amide into a zinc salt, e.g. zinc halide, which, together with the precipitating reagent, forms a sparingly soluble solid which can be readily removed and makes it possible to remove the zinc virtually quantitatively from the organic reaction solution.

In a particularly preferred embodiment of the invention, a proton donor is optionally added in small amounts based on the zinc compound in the removal of zinc from organic solutions comprising organozinc alkoxides and organozinc amides to completely precipitate the zinc. The addition of the proton donor converts the zinc compound, e.g. the alkyl- or arylzinc halide, to a hydrocarbon and a zinc salt (e.g. zinc dihalide). Any small amounts of water introduced into the reaction mixture thereby, in particular by using aqueous acids, can be distillatively removed without any problem in the further workup of the desired reaction product together with the organic solvent, for example in the form of an azeotrope.

When the compounds used as precipitating reagents are added before or during the formation of the zinc alkoxides or zinc amides, the compounds have to be inert under the conditions of the formation of the zinc alkoxides or zinc amides. The precipitating reagents must not react with the organozinc compounds, for example Reformatsky reagents, or diaryl/dialkylzinc compounds and must therefore contain no functional groups which are reactive under the given reaction conditions, for example aldehyde functions.

When Reformatsky reagents are used, owing to the basicity, the compounds used as precipitating reagents, when these are added before or during the formation of the zinc alkoxides or zinc amides, should have no acidic protons, in particular those having a pKa of less than 20, for example in the form of free amide functions NH—C=O or NH—SO2, or hydroxyl functions. The use in particular of large excesses of Reformatsky reagent is therefore avoided.

The nitrogen donors of the precipitating reagents used in the process according to the invention are typically N-heteroaromatics, amine, imine or enamine groups.

Preferred precipitating reagents are compounds which chelate zinc ions and have N-heteroaromatics and amine groups, more preferably compounds having at least two N-heteroaromatics or at least two secondary and/or tertiary amine groups.

Preferred precipitating reagents are in particular diamine compounds having N-heteroaromatics or secondary and/or tertiary amine groups, or compounds having at least two N-heteroaromatics or at least two amine groups.

Particularly suitable precipitating reagents for the process according to the invention are ethylenediamine and its derivatives, e.g. N,N'-dimethyl-, N,N,N'-trimethyl-, N,N,N',N'-tetramethylethylenediamine, N,N'-diethyl-, N,N,N'-triethyl-, N,N,N',N'-tetraethylethylenediamine, 1,2-diphenylethylenediamine and its derivatives, 1,2-di(tert-butyl)-1,2-ethylenediamine and its derivatives, N,N'-bis(1-phenylethyl)-1,2-ethylenediamine and its derivatives, diaminopropane and its derivatives, e.g. N,N'-dimethyl-, N,N,N'-trimethyl-, N,N,N',N'-tetramethyldiaminopropane, N,N'-bis(1-phenylethyl)-1,2-propylenediamine and its derivatives, diaminobutane and its derivatives, e.g. N,N'-dimethyl-, N,N,N'-trimethyl-, N,N,N',N'-tetramethyldiaminobutane, 2,3-dialkoxy-1,4-diaminobutane and its derivatives, piperazine and its derivatives, 1,4-diazabicyclo[2.2.2]octane and its derivatives, 3,7-diazabicyclo[3.3.1]nonane compounds, (−)-sparteine, 1,1'-binaphthyl-2,2'-diamine and its derivatives, 2,2'-bipyridyls, 1,10-phenanthrolene and its derivatives, pyrazine and its derivatives, 2,2'-bipyrrolidines, aminopyridines, aminoalkyl-substituted pyridines, aminopyrrolidines, aminoalkyl-substituted pyrrolidines, aminopiperidines, aminoalkyl-substituted piperidines, phenylenediamine and its derivatives, 1,2-diaminocyclohexane and its derivatives, amino-substituted dioxolanes, e.g. 4,5-di(aminomethyl)-2,2-dimethyldioxolane, 2-(aminomethyl)pyrrolidine and its derivatives, 2-(2-pyridyl)-pyrrolidine and its derivatives, or N,N'-bis(1-phenylethyl)-4,5-diamino-1,7-octadiene and its derivatives, diamino acid compounds, diamines which are derived from amino acids or diamines having ester, amide, ether, thioether, thioester, alkoxy, aryloxy, silyloxy, nitrile, acetal and ketal functions.

Suitable precipitating reagents for the process according to the invention are in particular ethylenediamine, N,N'-dimethyl-, N,N,N'-trimethyl-, N,N,N',N'-tetramethylethylenediamine, diaminopropane, N,N'-dimethyl-, N,N,N'-trimethyl-, N,N,N',N'-tetramethyldiaminopropane, diaminobutane, N,N'-dimethyl-, N,N,N'-trimethyl-, N,N,N',N'-tetramethyldiaminobutane, piperazine, 1,4-diazabicyclo[2.2.2]octane, (−)-sparteine, 1,1'-binaphthyl-2,2'-diamine, 2,2'-bipyridyl, pyrazine, 1,2-phenylenediamine, 1,2-diaminocyclohexane and N,N'-bis(1-phenylethyl)-4,5-diamino-1,7-octadiene.

In this connection, particularly preferred precipitating agents are ethylenediamine, diaminopropane, diaminobutane, piperazine, 1,4-diazabicyclo[2.2.2]octane, (−)-sparteine, 2,2'-bipyridyl and pyrazine.

The use of piperazine as a precipitating reagent provides sparingly soluble zinc salt complexes which can be readily filtered and make it possible to remove the zinc salt particularly effectively and virtually quantitatively from the organic reaction solution.

Useful alkylating or arylating, esterifying or silylating reagents for this purpose are any of the reagents well known to those skilled in the art from the prior art.

Preferred alkylating agents are methyl, ethyl, propyl, butyl or benzyl chloride, bromide or iodide, methyl, ethyl, propyl, butyl, benzyl tosylate and triflate, and dimethyl sulfate.

Preferred arylating reagents are fluorobenzene, 1-fluoro-4-trifluoromethylbenzene, 1-fluoronaphthalene, chlorobenzene, 1-chloro-4-trifluoromethylbenzene and 1-chloronaphthalene.

Preferred esterifying reagents are acetyl chloride or bromide, acetic anhydride, ketene and dimethyl and diethyl carbonate.

Preferred silylating reagents are trimethyl-, -ethyl-, -propyl-,-butylchlorosilane and tert-butyldimethylchlorosilane.

It has proven useful to react the zinc alkoxides or zinc amides, the silylating, acylating, alkylating or arylating reagents and the precipitating reagent in a molar ratio of 1:(1 to 10):(1 to 5), in particular 1:(1 to 3):(1 to 2), more preferably 1:(1 to 1.5):(1 to 1.5).

The reactions of the zinc alkoxides or zinc amides with the silylating, acylating, alkylating or arylating reagents and the compounds which contain at least two nitrogen donors and are used as precipitating agents are preferably carried out at temperatures of from −80 to +250° C., more preferably from −40 to +150° C., in particular from −20 to +80° C., optionally under reflux.

Preference is given to maintaining the temperature of the exothermic reaction at a predetermined value, optionally by cooling, during the addition of the silylating, acylating, alkylating or arylating reagents and the precipitating reagent. The upper temperature limit may be limited by the boiling point of the solvent used, for example tetrahydrofuran (b.p.: 66° C.) or ethyl acetate (b.p.: 78° C.). In the case of higher-boiling solvents, for example 1,4-dioxane (b.p.: 100–102° C.), the temperature of the reaction is preferably controlled by cooling.

The pressure range of the reaction is uncritical and may be varied within wide limits. The pressure is typically from 0.01 to 20 bar, but preference is given to carrying out the reaction under atmospheric pressure.

Preference is given to carrying out the reaction with inertization using protective gas, such as nitrogen or argon. The reaction may be carried out continuously or batchwise, preferably batchwise.

After the end of the addition of all constituents involved, the reaction is allowed to continue, preferably for another from 5 min to 15 h, more preferably from 20 min to 8 h, in particular from 30 min to 5 h, in order to complete the reaction and precipitation of the zinc salt complex.

In order to achieve a very substantial precipitation of the zinc salts after adding the precipitating reagent, in a preferred embodiment of the invention, it is necessary, especially when using solvents capable of coordinating to zinc ions, e.g. tetrahydrofuran or ethyl acetate, to very substantially distill the solvent out of the reaction mixture and replace it by comparatively uncoordinating solvent, e.g. pentane or benzene.

In a preferred embodiment of the invention, to substantially quantitatively precipitate out and remove the precipitated zinc salts by filtration or centrifugation, the temperature of the mixture is lowered. The temperatures are typically between 80 and +40° C., in particular between 40 and +15° C. In the case of distillitive workup, the solvents used are advantageously recovered in anhydrous form and may be reused for organozinc syntheses.

In one possible embodiment of the process according to the invention, the zinc compound, e.g. the alkyl- or arylzinc halide, is converted to a hydrocarbon and a zinc salt (e.g. zinc dihalide) by adding a proton donor.

The proton donor is added in small amounts of from 0.1 to 10 equivalents, preferably from 0.1 to 5 equivalents, more preferably from 0.5 to 2 equivalents, based on the zinc compound.

Useful proton donors are acids, aqueous acids or bases, water, alcohols or aqueous ammonia.

Suitable acids are Brönstedt acids, in particular strong acids, such as boric, tetrafluoroboric, nitric acid, nitrous acid, phosphoric acid, phosphorous acid, hypophosphorous acid, sulfuric acid, sulfurous acid, peroxosulfuric, hydrochloric, hydrofluoric, hydroiodic, hydrobromic, perchloric, hexafluorophosphoric acid, benzenesulfonic, p-toluenesulfonic, methanesulfonic, trifluoromethanesulfonic acid, carboxylic acids, such as chloroacetic, trichloroacetic, acetic, acrylic, benzoic, trifluoroacetic, citric, crotonic, formic, fumaric, maleic, malonic, gallic, itaconic, lactic, tartaric, oxalic, phthalic and succinic acid, and proton-containing salts, optionally in the form of aqueous solutions, such as hydrogencarbonate, hydrogensulfate, hydrogenphosphate, dihydrogenphosphate, in the form of their ammonium, sodium, potassium, magnesium and calcium salts, and also ammonium chloride and bromide. Proton-containing salts are optionally used directly in the form of their solids.

Suitable bases are ammonia and organic amines, such as alkyl-/arylamines and alkanolamines.

Suitable alcohols are primary, secondary and tertiary alcohols and also aromatic alcohols, such as methanol, ethanol, propanol, butanol, isopropanol, isobutanol, sec-butanol, tert-butanol and phenol.

In particular, hydrochloric acid, sulfuric acid, acetic acid, citric acid, sodium hydrogencarbonate, potassium hydrogencarbonate, sodium hydrogensulfate, potassium hydrogensulfate, ammonium chloride, aqueous ammonia, methanol, ethanol, isopropanol, water, preferably hydrochloric acid, sulfuric acid, acetic acid, sodium hydrogencarbonate, potassium hydrogencarbonate, ammonium chloride, methanol, ethanol and isopropanol are used. The acid may be used in concentrated form or in the form of a dilute aqueous solution.

When aqueous proton donors are used, the volumes are selected in a preferred embodiment of the process according to the invention in such a way that the proportion of water compared to organic solvent is very low, preferably from 0.05 to 25% by volume, more preferably from 0.05 to 20% by volume, in particular from 0.1 to 10% by volume.

After the precipitated zinc salt complex has been removed, any small amounts of water, added with the proton donor, for example aqueous hydrochloric acid or sulfuric acid, may be removed together with organic solvent, optionally in the form of an azeotrope. The solvents are thus obtained in anhydrous form and may be recycled into the synthetic process.

The advantages of the process according to the invention are in particular that the zinc salts are virtually completely precipitated and removed directly from the reaction solutions in organic solvent without preceding hydrolytic workup. In contrast to the prior art processes, in which the zinc is precipitated in principle out of aqueous zinc-containing solutions and in which, even after removal of precipitates, large amounts of wastewater contaminated with heavy metals remain, which have to be worked up in a costly and inconvenient manner, the process according to the invention results in no zinc-containing aqueous phase and no wastewater which usually also has to be freed of organic impurities in a costly and inconvenient manner. The process according to the invention is therefore a very advantageous process for economic and ecological reasons, in particular because amounts of waste are reduced, especially on application on the industrial scale.

In addition, the organic solvents used are recovered in anhydrous form and may advantageously be reused in the organozinc synthetic processes. An often very costly and inconvenient further treatment of the recovered solvents to remove water is unnecessary, which makes the process according to the invention particularly economically viable.

In contrast to existing processes, there is no treatment with precipitating agents, e.g. sulfide, polysulfide, polysulfane or trithiocarbonate. Thus the reaction products form no undesired by-products and impurities under the conditions of the reaction with the compounds used as precipitating reagents. The quality of the products prepared by the invention is particularly high, which has an advantageous effect on the economic viability of the overall preparative process.

The precipitating reagents used can also be very easily recovered from their zinc salt complexes in high yields and reused, which makes the process according to the invention, especially when carried out on the industrial scale, particularly cost-effective and economical.

To this end, the zinc salt complex is suspended in a suitable solvent, such as toluene, xylene, heptane or dibutyl ether, and heated in the presence of a hydroxide or oxide base, e.g. solid sodium hydroxide, without using water as solvent, to release the precipitating reagent from the complex and form sparingly soluble zinc salt, e.g. zinc hydroxide. After filtration, the precipitating reagent is recovered after removing solvent. The precipitating reagent and the anhydrous solvent are particularly advantageously recycled into the process, which makes the process according to the invention particularly economical from an industrial point of view and environmentally friendly, owing to the protection of resources.

Preferred solvents for the recovery are in particular ethers, hydrocarbons and hydrocarbon-substituted silanes and siloxanes. Useful ethers are mono- and polyethers, preferably symmetrical and unsymmetrical di-$C_1$–$C_{10}$-hydrocarbon ethers, for example dibutyl ether, tetrahydrofuran, dihexyl ether, diphenyl ether, anisole, phenetole or cyclic ethers, such as coumarone and tetrahydrofuran. Examples of polyethers include polyethylene glycol dimethyl ether and polyethylene glycol diethyl ether. Preferred aromatic or aliphatic hydrocarbons are $C_1$–$C_{20}$-hydrocarbons and their mixtures, such as toluene, hylbenzene, propylbenzene, isopropylbenzene, butylbenzene, xylene, xylene isomer mixtures, trimethylbenzene, heptane, octane, isooctane, nonane, nonane fraction, cycloheptane, cyclooctane, dimethylcyclohexane, ethylcyclohexane, propylcyclohexane, butylcyclohexane, petroleum and paraffin. Hydrocarbon-substituted silanes and siloxanes are hydrocarbons in which one or more methylene groups may also be replaced by dialkylsilyl or dialkylsiloxy groups. Preferred examples are tetraethylsilane, tetrapropylsilane, tetrabutylsilane, dimethyldiphenylsilane and polydimethylsiloxane. Preference is given to solvents or solvent mixtures having a boiling point or boiling range of up to 250° C. at 0.1 MPa.

Particularly suitable hydroxide and oxide bases for the recovery are the hydroxides and oxides of lithium, sodium, potassium, magnesium and calcium. Preference is given to using alkali metal and alkaline earth metal hydroxides, in particular sodium hydroxide and potassium hydroxide. The solid alkali metal and alkaline earth metal bases are used in the form of platelets, flakes, spheres, beads, prills, microprills or in pulverulent form, preferably in pulverulent form and as prills or microprills.

The recovery process is preferably carried out at temperatures of from 30 to 300° C., in particular from 60 to 200° C. During the reaction, the temperature is maintained at the predetermined value. Optionally, the upper temperature limit may be limited by the boiling point of the inert solvent used, e.g. di-n-butyl ether (b.p.: 140–143° C.), heptane fraction (b.p.: 93–99° C.) or xylene isomer mixture (b.p.: 137–143° C.).

For example, piperazine and (−)-sparteine can be obtained in a very simple manner in anhydrous form from their zinc salt complexes by treating with sodium hydroxide in toluene, hexane or heptane as solvent in very high yields of up to >95% and reused. Zinc hydroxide-containing anhydrous solids obtained in this process can be particularly effectively removed by filtration, advantageously transported in anhydrous form and fed to zinc recycling.

When using piperazine and (−)-sparteine as diamine precipitating agents, recovery can in particular be carried out in high yields.

In particular, when the organozinc reaction mixture is reacted with trialkylhalosilane, in particular trimethylchlorosilane, piperazine and (−)-sparteine can be isolated in very high yields as solids in the form of a zinc salt, removed by filtration and >95% recovered. In this way, the zinc is virtually completely removed from the reaction solution. The simple and effective recovery of piperazine and (−)-sparteine, in particular piperazine, makes the process according to the invention particularly economical.

DETAILED DESCRIPTION OF PREFERRED EMBODIMENTS

In the examples which follow, unless otherwise stated, all amounts and percentages are based on weight, all pressures are 0.10 MPa (abs.) and all temperatures 20° C.

EXAMPLE 1

Removal of Zinc when Preparing Methyl 3-trimethylsiloxy-3-(2"-phenylethyl)caproate by Reformatsky Reaction Using Piperazine as the Precipitating Agent At room temperature, a three-neck flask equipped with a reflux condenser, internal thermometer, dropping funnel and stirrer under protective nitrogen gas was initially charged with 4.6 g of zinc powder (71 mmol) in 40 ml of ethyl acetate. After 1.13 ml of trimethylchlorosilane had been added, the mixture was heated to 50° C. for 15 min and 10 g of 1-phenylhexan-3-one (57 mmol, prepared by base-catalyzed aldol condensation of benzaldehyde and pentan-2-one and subsequent hydrogenation of the 1-phenylhex-1-en-3-one obtained) were added undiluted. Subsequently, 10.4 g of methyl bromoacetate (68 mmol) were added dropwise within 5 min and the temperature was maintained at 60° C. by external cooling. The mixture was then stirred at 55° C. for 10 min (formation of the zinc alkoxide). After cooling to 10° C., 7.4 g of trimethylchlorosilane (68 mmol) were added and the mixture was heated to 40° C. for 30 min. At 20° C., 7.4 g of piperazine (85 mmol) were subsequently added as a solid. The mixture was then stirred at 50° C. for 3 h. After the ethyl acetate solvent had been virtually completely distilled off (recovery of the anhydrous solvent), 40 ml of pentane were added, the suspension was cooled to −20° C. and stirred for 1 h, and the solid formed (complex of zinc bromide chloride and piperazine) was filtered off. The solid was washed three times with 10 ml of pentane. Pentane was distilled off under reduced pressure (recovery of pentane) and the desired product methyl 3-trimethylsiloxy-3-(2"-phenylethyl)caproate was obtained in a yield of 17.4 g (95% of theory) and a purity of >97% (HPLC). The zinc content of the product was 20 ppm (ICP).

EXAMPLE 2

Removal of Zinc when Preparing Methyl 3-trimethylsiloxy-3-(2"-phenylethyl)caproate by Reformatsky Reaction Using Piperazine as Precipitating Agent At room temperature, a three-neck flask equipped with a reflux condenser, internal thermometer, dropping funnel and stirrer under protective nitrogen gas was initially charged with 4.6 g of zinc powder (71 mmol) in 40 ml of tetrahydrofuran. After 1.13 ml of trimethylchlorosilane had been added, the mixture was heated to 50° C. for 15 min and 10 g of 1-phenylhexan-3-one (57 mmol, prepared by base-catalyzed aldol condensation of benzaldehyde and pentan-2-one and subsequent hydrogenation of the 1-phenylhex-1-en-3-one obtained) were added undiluted. Subsequently, 10.4 g of methyl bromoacetate (68 mmol) were added dropwise within 5 min and the temperature was maintained at 50° C. by external cooling. The mixture was then stirred at 50° C. for 10 min (formation of the zinc alkoxide). After cooling to 10° C., 7.4 g of trimethylchlorosilane (68 mmol) were added and the mixture was heated to 40° C. for 30 min. At 20° C., 7.4 g of piperazine (85 mmol), dissolved in 90 ml of tetrahydrofuran, were subsequently added, and a precipitate formed immediately. 90 ml of tetrahydrofuran were then distilled off (recovery of the anhydrous solvent) and the precipitate formed (complex of zinc bromide chloride and piperazine) was filtered off. The precipitate was washed twice with 30 ml of tetrahydrofuran each time, and tetrahydrofuran was subsequently distilled off completely under reduced pressure (recovery of the anhydrous solvent). The residue was admixed with 40 ml of pentane, cooled to −20° C., stirred for 60 min, and residues of solid were filtered off. Pentane was distilled off under reduced pressure (recovery of pentane) and the desired product methyl 3-trimethylsiloxy-3-(2"-phenylethyl)caproate was obtained in a yield of 16.7 g (91% of theory) and a purity of >97% (HPLC). The zinc content of the product was 5 ppm (ICP).

EXAMPLE 3

Removal of Zinc when Preparing Methyl 3-trimethylsiloxy-3-(2"-phenylethyl)caproate by Reformatsky Reaction Using 1,4-diazabicyclo[2.2.2]octane as Precipitating Agent At room temperature, a three-neck flask equipped with a reflux condenser, internal thermometer, dropping funnel and stirrer under protective nitrogen gas was initially charged with 4.6 g of zinc powder (71 mmol) in 40 ml of tetrahydrofuran. After 1.13 ml of trimethylchlorosilane had been added, the mixture was heated to 50° C. for 15 min and 10 g of 1-phenylhexan-3-one (57 mmol, prepared by base-catalyzed aldol condensation of benzaldehyde and pentan-2-one and subsequent hydrogenation of the 1-phenylhex-1-en-3-one obtained) were added undiluted. Subsequently, 10.4 g of methyl bromoacetate (68 mmol) were added dropwise within 5 min and the temperature was maintained at 50° C. by external cooling. The mixture was then stirred at 50° C. for 10 min (formation of the zinc alkoxide). After cooling to 10° C., 7.4 g of trimethylchlorosilane (68 mmol) were added and the mixture was heated to 40° C. for 30 min. At 20° C., 9.6 g of 1,4-diazabicyclo[2.2.2]octane (85 mmol), dissolved in 55 g of tetrahydrofuran, were added, and the precipitate formed immediately. The precipitate formed (complex of zinc bromide chloride and 1,4-diazabicyclo[2.2.2]octane) was then filtered off. The precipitate was washed twice with 30 ml of tetrahydrofuran each time, and tetrahydrofuran was subsequently distilled off completely under reduced pressure (recycling of anhydrous solvent). The residue was admixed with 50 ml of pentane, cooled to −20° C., stirred for 60 min, and residues of solid were filtered off. Pentane was distilled off under reduced pressure (recovery of pentane) and the desired product 3-trimethylsiloxy-3-(2"-phenylethyl)caproate was obtained in a yield of 16 g (87% of theory) and a purity of >97% (HPLC). The zinc content of the product was 70 ppm (ICP).

EXAMPLE 4
Removal of Zinc when Preparing Methyl 3-trimethylsiloxy-3-(2'-phenylethyl)caproate by Reformatsky Reaction Using Piperazine as Precipitating Agent At room temperature, a three-neck flask equipped with a reflux condenser, internal thermometer, dropping funnel and stirrer under protective nitrogen gas was initially charged with 4.6 g of zinc powder (71 mmol) in 40 ml of ethyl acetate. After 1.13 ml of trimethylchlorosilane had been added, the mixture was heated to 50° C. for 15 min and 10 g of 1-phenylhexan-3-one (57 mmol, prepared by base-catalyzed aldol condensation of benzaldehyde and pentan-2-one and subsequent hydrogenation of the 1-phenylhex-1-en-3-one obtained) were added undiluted. Subsequently, 10.4 g of methyl bromoacetate (68 mmol) were added dropwise within 5 min and the temperature was maintained at 40° C. by external cooling. The mixture was then stirred at 40° C. for 10 min (formation of the zinc alkoxide). After cooling to 10° C., 7.4 g of trimethylchlorosilane (68 mmol) were added and the mixture was heated to 40° C. for 30 min. After the ethyl acetate solvent had been removed (recovery of the anhydrous solvent), 40 ml of pentane were added and 7.4 g of solid piperazine (85 mmol) were subsequently added at 20° C. The mixture was then stirred at 50° C. for 6 h, and the suspension was cooled to −20° C., stirred for 1 h and solid formed (complex of zinc bromide chloride and piperazine) was filtered off. The solid was washed three times with 10 ml of pentane. The mixture was filtered again, pentane was filtered off under reduced pressure (recovery of pentane) and the desired product methyl 3-trimethylsiloxy-3-(2"-phenylethyl)caproate was obtained in a yield of 15.8 g (86% of theory) and a purity of >97% (HPLC). The zinc content of the product was 40 ppm (ICP).

EXAMPLE 5
Removal of Zinc when Preparing Methyl 3-trimethylsiloxy-3-(2'-phenylethyl)caproate by Reformatsky Reaction Using N,N,N",N"-tetramethylethylenediamine as Precipitating Agent At room temperature, a three-neck flask equipped with a reflux condenser, internal thermometer, dropping funnel and stirrer under protective nitrogen gas was initially charged with 4.6 g of zinc powder (71 mmol) in 40 ml of tetrahydrofuran. After 1.13 ml of trimethylchlorosilane had been added, the mixture was heated to 50° C. for 15 min and 10 g of 1-phenylhexan-3-one (57 mmol, prepared by base-catalyzed aldol condensation ofenzaldehyde and pentan-2-one and subsequent hydrogenation of the 1-phenylhex-1-en-3-one obtained) were added undiluted. Subsequently, 10.4 g of methyl bromoacetate (68 mmol) were added dropwise within 5 min and the temperature was maintained at 50° C. by external cooling. The mixture was then stirred at 50° C. for 10 min (formation of the zinc alkoxide). After cooling to 10° C., 7.4 g of trimethylchlorosilane (68 mmol) were added and the mixture was heated to 40° C. for 30 min. The mixture was then stirred at 40° C. for 30 min. At 20° C., 9.9 g of N,N,N",N"-tetramethylethylenediamine (85 mmol) were subsequently added undiluted. The mixture was then stirred at 50° C. for 3 h. After the tetrahydrofuran solvent had been virtually completely distilled off (recycling of anhydrous solvent), 40 ml of pentane were added, the suspension was cooled to −20° C. and stirred for 1 h, and solid formed (complex of zinc bromide chloride and N,N,N",N"-tetramethylethylenediamine) was filtered off. The solid was washed three times with 10 ml of pentane. Pentane was distilled off under reduced pressure (recovery of pentane) and the desired product methyl 3-trimethylsiloxy-3-(2"-phenylethyl) caproate was obtained in a yield of 16.9 g (92% of theory) and a purity of >97% (HPLC). The zinc content of the product is 120 ppm (ICP).

EXAMPLE 6
Removal of Zinc when Preparing Methyl 3-trimethylsiloxy-3-phenylpropionate by Reformatsky Reaction Using Ethylenediamine as Precipitating Agent At room temperature, a three-neck flask equipped with a reflux condenser, internal thermometer, dropping funnel and stirrer under protective nitrogen gas was initially charged with 4.6 g of zinc powder (71 mmol) in 40 ml of tetrahydrofuran. After 1.13 ml of trimethylchlorosilane had been added, the mixture was heated to 50° C. for 15 min, and 6.5 g of benzaldehyde (57 mmol) were added undiluted. 10.4 g of methyl bromoacetate (68 mmol) were subsequently added dropwise at 45° C. within 5 min while maintaining the temperature at 50° C. by external cooling. The mixture was then stirred at 50° C. for 10 min (formation of the zinc alkoxide). After cooling to 10° C., 7.4 g of trimethylchlorosilane (68 mmol) were added and the mixture was heated at 40° C. for 30 min. At 20° C., 5.1 g of ethylenediamine (85 mmol) were subsequently added and diluted. The mixture was then stirred at 50° C. for 3 h. After the tetrahydrofuran solvent had been virtually completely distilled off (recovery of the anhydrous solvent), 40 ml of pentane were added, the suspension was cooled to −20° C., stirred for 1 h and solid formed (complex of zinc bromide chloride and ethylenediamine) was filtered off. The solid was washed three times with 10 ml of cold pentane. Pentane was distilled off under reduced pressure (recovery of pentane) and the desired product methyl 3-trimethylsiloxy-3-phenylpropionate was obtained in a yield of 13.1 g (91% of theory) and a purity of >95% (HPLC). The zinc content of the product is 110 ppm (ICP).

EXAMPLE 7
Removal of Zinc when Preparing Methyl 3-acetoxy-3-phenylpropionate by Reformatsky Reaction Using Piperazine as Precipitating Agent At room temperature, a three-neck flask equipped with a reflux condenser, internal thermometer, dropping funnel and stirrer under protective nitrogen gas was initially charged with 4.6 g of zinc powder (71 mmol) in 40 ml of tetrahydrofuran. After 0.8 ml of trimethylchlorosilane had been added, the mixture was heated to 50° C. for 15 min, and 6.5 g of benzaldehyde (57 mmol) were added undiluted. 10.4 g of methyl bromoacetate (68 mmol) were subsequently added dropwise at 45° C. within 5 min while maintaining the temperature at 50° C. by external cooling. The mixture was then stirred at 50° C. for 10 min (formation of the zinc alkoxide). After cooling to 10° C, 5.3 g of acetyl chloride (68 mmol) were added and the mixture was heated at 40° C. for 30 min. At 20° C., 7.4 g of piperazine (85 mmol) were subsequently added as solid. The mixture was then stirred at 50° C. for 3 h. After the tetrahydrofuran solvent had been virtually completely distilled off (recovery of the anhydrous solvent), 40 ml of pentane were added, the suspension was cooled to −20° C., stirred for 1 h and solid formed (complex of zinc bromide chloride and piperazine) was filtered off. The solid was washed three times with 10 ml of cold pentane each time. Pentane was distilled off under reduced pressure (recovery of pentane) and the desired product methyl 3-acetoxy-3-phenylpropionate was obtained in a yield of 11.3 g (89% of theory) and a purity of >95% (HPLC). The zinc content of the product is 20 ppm (ICP).

EXAMPLE 8

Removal of Zinc when Preparing (S)-(+)-3-undecanol by Alkylating Diethyl Zinc Using Piperazine as Precipitating Agent At room temperature, a three-neck flask equipped with a reflux condenser, internal thermometer, dropping funnel and stirrer under protective nitrogen gas was initially charged with 0.16 g of (1S,2R)-(−)-2-(N,N-di-n-butylamino)-1-phenylpropan-1-ol (0.6 mmol) in 18 ml of hexane and 1.4 g of nonanal (10 mmol) were added. The mixture was stirred for 15 min and cooled to 0° C. 12 ml of a 1 M solution of diethylzinc in hexane (12 mmol) were added to this mixture, and the mixture was stirred at 0° C. for 14 h. 1.6 g of trimethylchlorosilane (15 mmol) were then added, and the mixture was heated to 40° C. for 30 min. 1.3 g of piperazine (15 mmol) were then added and the mixture was stirred for 60 min. At −10° C., 2.3 ml of 6 N hydrochloric acid were subsequently added and the mixture was stirred at 15° C. for 30 min. After water together with hexane had been distilled off, 40 ml of pentane were added, the suspension was cooled to −20° C. and solid formed was filtered off. The solid was washed three times with 10 ml of cold pentane. Pentane was distilled off under reduced pressure (recovery of pentane) and the desired product (S)-(+)-3-nonanol was obtained in a yield of 1.6 g (89% of theory) and a purity of >95% and 87% ee (HPLC). The zinc content of the product was 30 ppm (ICP).

COMPARATIVE EXAMPLE 9

Removal of Zinc when Preparing Methyl 3-trimethylsiloxy-3-(2"-phenylethyl)caproate by Reformatsky Reaction Using triethylamine as Precipitating Agent At room temperature, a three-neck flask equipped with a reflux condenser, internal thermometer, dropping funnel and stirrer under protective nitrogen gas was initially charged with 4.6 g of zinc powder (71 mmol) in 40 ml of tetrahydrofuran. After 0.8 ml of trimethylchlorosilane had been added, the mixture was heated to 50° C. for 15 min and 10 g of 1-phenylhexan-3-one (57 mmol, prepared by base-catalyzed aldol condensation of benzaldehyde and pentan-2-one and subsequent hydrogenation of the 1-phenylhex-1-en-3-one obtained) were added undiluted. Subsequently, 10.4 g of methyl bromoacetate (68 mmol) were added dropwise within 5 min and the temperature was maintained at 60° C. by external cooling. The mixture was then stirred at 55° C. for 10 min (formation of the zinc alkoxide). After cooling to 10° C., 7.4 g of trimethylchlorosilane (68 mmol) were added and the mixture was heated to 40° C. for 30 min. At 20° C., 19.6 ml of triethylamine (142 mmol) were subsequently added undiluted, and no precipitate was formed. The clear mixture was then stirred at 50° C. for 3 h. After the tetrahydrofuran solvent had been virtually completely distilled off (recovery of the anhydrous solvent), 40 ml of pentane were added, the suspension was cooled to −20° C. and solid formed (complex of zinc bromide chloride and triethylamine) was filtered off. The solid was washed three times with 10 ml of pentane. Pentane was distilled off under reduced pressure (recovery of pentane) and the desired product methyl 3-trimethylsiloxy-3-(2"-phenylethyl)caproate was obtained in a yield of 15.6 g (85% of theory) and a purity of >95% (HPLC). The zinc content of the product was >0.5% (ICP).

COMPARATIVE EXAMPLE 10

Removal of Zinc when Preparing Methyl 3-trimethylsiloxy-3-(2'-phenylethyl)caproate by Reformatsky Reaction Using Pyridine as Precipitating Agent At room temperature, a three-neck flask equipped with a reflux condenser, internal thermometer, dropping funnel and stirrer under protective nitrogen gas was initially charged with 4.6 g of zinc powder (71 mmol) in 40 ml of tetrahydrofuran. After 0.8 ml of trimethylchlorosilane had been added, the mixture was heated to 50° C. for 15 min and 10 g of 1-phenylhexan-3-one (57 mmol, prepared by base-catalyzed aldol condensation of benzaldehyde and pentan-2-one and subsequent hydrogenation of the 1-phenylhex-1-en-3-one obtained) were added undiluted. Subsequently, 10.4 g of methyl bromoacetate (68 mmol) were added dropwise within 5 min and the temperature was maintained at 60° C. by external cooling. The mixture was then stirred at 55° C. for 10 min (formation of the zinc alkoxide). After cooling to 10° C., 7.4 g of trimethylchlorosilane (68 mmol) were added and the mixture was heated to 40° C. for 30 min. At 20° C., 11.5 g of pyridine (145 mmol) were subsequently added undiluted, and a precipitate was formed. The suspension was then stirred at 50° C. for 2 h. After the tetrahydrofuran solvent had been virtually completely distilled off (recovery of the anhydrous solvent), 50 ml of pentane were added, the suspension was cooled to −20° C. and solid formed (complex of zinc bromide chloride and pyridine) was filtered off. The solid was washed three times with 10 ml of pentane. Pentane was distilled off under reduced pressure (recovery of pentane) and the desired product methyl 3-trimethylsiloxy-3-(2'-phenylethyl)caproate was obtained (the product contains 20 mol % of pyridine). The zinc content of the product was 900 ppm (ICP).

EXAMPLE 11

Recovery of (−)-sparteine from Precipitated (−)-sparteine-zinc Bromide Chloride Complex (Obtained in a Similar Manner to Example 6)

At room temperature, a three-neck flask equipped with a reflux condenser, internal thermometer and stirrer under protective nitrogen gas was initially charged with 160 g of (−)-sparteine-zinc bromide chloride complex (obtained according to Example 6) (0.385 mol) and 62 g of sodium hydroxide microprills (1.54 mol) suspended in 350 ml of heptane. The mixture was heated to 95° C. for 4 h, subsequently cooled to 20° C. and the solid was filtered off. The solid was washed three times with 30 ml of heptane. Heptane was distilled off under reduced pressure (recovery of heptane) and (−)-sparteine was obtained in a yield of 87.5 g (97% of theory) and a purity of >97% (GC). Purification of (−)-sparteine is possible, if desired, by distillation (boiling point: 117° C./0.067 mbar).

Accordingly, while a few embodiments of the present invention have been shown and described, it is to be understood that many changes and modifications may be made thereunto without departing form the spirit and scope of the invention as defined in the appended claims.

What is claimed is:

1. A process for removing zinc from an organic solution containing a zinc alkoxide or a zinc amide, comprising the steps of admixing the organic solution with an agent selected from the group consisting of an alkylating agent, in arylating agent, an acylating agent and a silylating agent in the presence of a precipitating reagent having at least two nitrogen donors; and subsequently removing a precipitated solid.

2. A process as claimed in claim 1, comprising
using a solution comprising halozinc alkoxides or halozinc amides to carry out the process.

3. A process as claimed in claim 1, comprising
using a solution comprising organozinc alkoxides or organozinc amides to carry out the process.

4. A process as claimed in claim 1,
which is carried out using a solution containing organozinc alkoxides or organozinc amides and additionally containing addition of another proton donor selected from the group consisting of acids, aqueous acids, bases, water, alcohols, and aqueous ammonia.

5. A process as claimed in claim 1,
wherein the precipitating reagent contains at least two N-heteroaromatics or at least two amine groups.

6. A process as claimed in claim 1,
wherein the precipitating reagent is selected from the group consisting of ethylenediamine, N,N"-dimethyl-, N,N,N''-trimethyl-, N,N,N'',N''-tetramethylethylenediamine, diaminopropane, N,N''-dimethyl-, N,N,N'-'-trimethyl-, N,N,N'',N''-tetramethyldiaminopropane, diaminobutane, N,N''-dimethyl-, N,N,N''-trimethyl-, N,N,N'',N'-''-tetramethyldiaminobutane, piperazine, 1,4-diazabicyclo[2.2.2]octane, (-)-sparteine, 1,1''-binaphthyl-2,2''-diamine, 2,2''-bipyridyl, pyrazine, 1,2-phenylenediamine, 1,2-diaminocyclohexane and N,N''-bis(1-phenylethyl)-4,5-diamino-1,7-octadiene.

7. A process as claimed in claim 1, comprising
adding trimethylchlorosilane to the solution as a silylating agent.

8. A process as claimed in claim 1,
wherein the precipitating reagent is recovered from removed solid.

9. A process as claimed in claim 1,
wherein the precipitating reagent is recovered from removed solid by adding a hydroxide or oxide base in a solvent.

10. A process as claimed in claim 3,
wherein the precipitating reagent is reacted with the organozinc alkoxide or organozinc amide and the silylating, acylating, alkylating or arylating agent in a molar ratio of (1 to 1.5):1:(1 to 1.5).

* * * * *